US009345534B2

(12) United States Patent
Artale et al.

(10) Patent No.: US 9,345,534 B2
(45) Date of Patent: May 24, 2016

(54) VESSEL SEALING INSTRUMENT

(75) Inventors: Ryan C. Artale, Boulder, CO (US); Tony Moua, Broomfield, CO (US); Robert M. Sharp, Boulder, CO (US)

(73) Assignee: Covidien LP, Mansfield, MA (US)

(*) Notice: Subject to any disclaimer, the term of this patent is extended or adjusted under 35 U.S.C. 154(b) by 660 days.

(21) Appl. No.: 13/415,471

(22) Filed: Mar. 8, 2012

(65) Prior Publication Data

US 2012/0172873 A1 Jul. 5, 2012

Related U.S. Application Data

(63) Continuation-in-part of application No. 12/897,346, filed on Oct. 4, 2010.

(51) Int. Cl.

| | |
|---|---|
| ***A61B 18/14*** | (2006.01) |
| *A61B 18/00* | (2006.01) |
| *A61B 19/00* | (2006.01) |

(52) U.S. Cl.

CPC ..... *A61B 18/1442* (2013.01); *A61B 2018/0063* (2013.01); *A61B 2018/00404* (2013.01); *A61B 2018/00601* (2013.01); *A61B 2018/00916* (2013.01); *A61B 2018/1412* (2013.01); *A61B 2018/1455* (2013.01);

(Continued)

(58) Field of Classification Search

CPC ................. A61B 2018/1455; A61B 2018/146; A61B 18/1445; A61B 2018/00404; A61B 2018/00601; A61B 2018/00297; A61B 2018/0063; A61B 2018/00708; A61B 2018/00916

USPC ............................ 606/41, 42, 45, 48–52, 171

See application file for complete search history.

(56) References Cited

U.S. PATENT DOCUMENTS

| | | | |
|---|---|---|---|
| 3,100,489 | A | 8/1963 | Bagley |
| D249,549 | S | 9/1978 | Pike |
| D263,020 | S | 2/1982 | Rau, III |

(Continued)

FOREIGN PATENT DOCUMENTS

| | | | |
|---|---|---|---|
| CN | 86105764 | A | 1/1987 |
| CN | 101507635 | A | 8/2009 |

(Continued)

OTHER PUBLICATIONS

U.S. Appl. No. 08/926,869, filed Sep. 10, 1997, James G. Chandler.

(Continued)

*Primary Examiner* — Michael Peffley
*Assistant Examiner* — Thomas Giuliani

(57) ABSTRACT

A bipolar electrosurgical instrument includes a housing and an elongated shaft. An end effector is coupled to a distal end of the elongated shaft. A handle assembly includes a movable handle movable relative to a fixed handle for effecting movement of the jaw members from a first position to a second position. Each jaw member is configured to connect to a source of electrosurgical energy. A switch is disposed on the fixed handle and configured to be depressed between a first position and at least one subsequent position upon biasing engagement with a switch engaging surface disposed on the movable handle. The first position of the switch causes the relay of information to the user corresponding to a desired pressure on tissue grasped between the jaw members and the at least one subsequent position is configured to activate the source of electrosurgical energy.

7 Claims, 9 Drawing Sheets

10 100 110 120 67a 16a 12a 66 67b 16b 17 14a 17a 45 45b 54 51 12b 50 23b 23a 19 14b 13 15a 15 202c 202b 202a 200 210

(52) U.S. Cl.
CPC .. *A61B 2019/2292* (2013.01); *A61B 2019/304* (2013.01); *A61B 2019/465* (2013.01)

(56) References Cited

U.S. PATENT DOCUMENTS

| | | | | |
|---|---|---|---|---|
| D295,893 | S | 5/1988 | Sharkany et al. | |
| D295,894 | S | 5/1988 | Sharkany et al. | |
| D298,353 | S | 11/1988 | Manno | |
| D299,413 | S | 1/1989 | Decarolis | |
| 5,122,139 | A | 6/1992 | Sutter | |
| 5,215,101 | A | 6/1993 | Jacobs et al. | |
| D343,453 | S | 1/1994 | Noda | |
| 5,324,289 | A | 6/1994 | Eggers et al. | |
| D348,930 | S | 7/1994 | Olson | |
| D349,341 | S | 8/1994 | Lichtman et al. | |
| D354,564 | S | 1/1995 | Medema | |
| D358,887 | S | 5/1995 | Feinberg | |
| 5,443,480 | A | 8/1995 | Jacobs et al. | |
| 5,472,443 | A | 12/1995 | Cordis et al. | |
| 5,542,945 | A | 8/1996 | Fritzsch | |
| D384,413 | S | 9/1997 | Zlock et al. | |
| H1745 | H | 8/1998 | Paraschac | |
| 5,797,938 | A | 8/1998 | Paraschac et al. | |
| 5,833,690 | A | 11/1998 | Yates et al. | |
| D402,028 | S | 12/1998 | Grimm et al. | |
| 5,849,022 | A | 12/1998 | Sakashita et al. | |
| 5,860,976 | A | 1/1999 | Billings et al. | |
| D408,018 | S | 4/1999 | McNaughton | |
| 5,891,140 | A | 4/1999 | Ginn | |
| 5,891,142 | A | 4/1999 | Eggers et al. | |
| 5,911,719 | A | 6/1999 | Eggers | |
| 5,925,043 | A | 7/1999 | Kumar et al. | |
| 5,957,923 | A | 9/1999 | Hahnen et al. | |
| D416,089 | S | 11/1999 | Barton et al. | |
| 6,010,516 | A | 1/2000 | Hulka | |
| D424,694 | S | 5/2000 | Tetzlaff et al. | |
| D425,201 | S | 5/2000 | Tetzlaff et al. | |
| 6,056,735 | A | 5/2000 | Okada | |
| 6,059,782 | A | 5/2000 | Novak et al. | |
| 6,123,701 | A | 9/2000 | Nezhat | |
| H1904 | H | 10/2000 | Yates et al. | |
| 6,206,877 | B1 | 3/2001 | Kese et al. | |
| 6,235,027 | B1 | 5/2001 | Herzon | |
| 6,270,497 | B1 | 8/2001 | Sekino et al. | |
| D449,886 | S | 10/2001 | Tetzlaff et al. | |
| D453,923 | S | 2/2002 | Olson | |
| D454,951 | S | 3/2002 | Bon | |
| D457,958 | S | 5/2002 | Dycus et al. | |
| D457,959 | S | 5/2002 | Tetzlaff et al. | |
| H2037 | H | 7/2002 | Yates et al. | |
| 6,443,952 | B1 | 9/2002 | Mulier et al. | |
| D465,281 | S | 11/2002 | Lang | |
| D466,209 | S | 11/2002 | Bon | |
| 6,533,778 | B2 | 3/2003 | Herzon | |
| 6,682,527 | B2 | 1/2004 | Strul | |
| D493,888 | S | 8/2004 | Reschke | |
| 6,776,780 | B2 | 8/2004 | Mulier et al. | |
| D496,997 | S | 10/2004 | Dycus et al. | |
| 6,802,843 | B2 | 10/2004 | Truckai et al. | |
| D499,181 | S | 11/2004 | Dycus et al. | |
| D502,994 | S | 3/2005 | Blake, III | |
| D509,297 | S | 9/2005 | Wells | |
| 6,964,662 | B2 | 11/2005 | Kidooka | |
| D525,361 | S | 7/2006 | Hushka | |
| 7,083,613 | B2 | 8/2006 | Treat | |
| D531,311 | S | 10/2006 | Guerra et al. | |
| 7,131,970 | B2 | 11/2006 | Moses et al. | |
| D533,274 | S | 12/2006 | Visconti et al. | |
| D533,942 | S | 12/2006 | Kerr et al. | |
| D535,027 | S | 1/2007 | James et al. | |
| D538,932 | S | 3/2007 | Malik | |
| D541,418 | S | 4/2007 | Schechter et al. | |
| D541,611 | S | 5/2007 | Aglassinger | |
| D541,938 | S | 5/2007 | Kerr et al | |
| 7,211,079 | B2 | 5/2007 | Treat | |
| D545,432 | S | 6/2007 | Watanabe | |
| D547,154 | S | 7/2007 | Lee | |
| 7,252,667 | B2 | 8/2007 | Moses et al. | |
| 7,267,677 | B2 | 9/2007 | Johnson et al. | |
| 7,329,256 | B2 | 2/2008 | Johnson et al. | |
| D564,662 | S | 3/2008 | Moses et al. | |
| D567,943 | S | 4/2008 | Moses et al. | |
| D575,395 | S | 8/2008 | Hushka | |
| D575,401 | S | 8/2008 | Hixson et al. | |
| D582,038 | S | 12/2008 | Swoyer et al. | |
| 7,470,272 | B2 | 12/2008 | Mulier et al. | |
| 7,500,975 | B2 | 3/2009 | Cunningham et al. | |
| 7,513,898 | B2 | 4/2009 | Johnson et al. | |
| D617,900 | S | 6/2010 | Kingsley et al. | |
| D617,901 | S | 6/2010 | Unger et al. | |
| D617,902 | S | 6/2010 | Twomey et al. | |
| D617,903 | S | 6/2010 | Unger et al. | |
| D618,798 | S | 6/2010 | Olson et al. | |
| 7,744,615 | B2 | 6/2010 | Couture | |
| D621,503 | S | 8/2010 | Otten et al. | |
| 7,811,283 | B2 | 10/2010 | Moses et al. | |
| D627,462 | S | 11/2010 | Kingsley | |
| D628,289 | S | 11/2010 | Romero | |
| D628,290 | S | 11/2010 | Romero | |
| D630,324 | S | 1/2011 | Reschke | |
| 7,887,536 | B2 | 2/2011 | Johnson et al. | |
| 7,896,878 | B2 | 3/2011 | Johnson et al. | |
| 7,909,823 | B2 | 3/2011 | Moses et al. | |
| 7,922,718 | B2 | 4/2011 | Moses et al. | |
| D649,249 | S | 11/2011 | Guerra | |
| D649,643 | S | 11/2011 | Allen, IV et al. | |
| 8,497,436 | B2 | 7/2013 | Palmer et al. | |
| 2004/0092927 | A1* | 5/2004 | Podhajsky et al. | 606/42 |
| 2006/0074417 | A1 | 4/2006 | Cunningham et al. | |
| 2006/0167452 | A1 | 7/2006 | Moses et al. | |
| 2007/0088356 | A1 | 4/2007 | Moses et al. | |
| 2007/0106297 | A1 | 5/2007 | Dumbauld et al. | |
| 2008/0114356 | A1 | 5/2008 | Johnson et al. | |
| 2008/0215048 | A1* | 9/2008 | Hafner et al. | 606/42 |
| 2008/0319442 | A1 | 12/2008 | Unger et al. | |
| 2009/0012520 | A1 | 1/2009 | Hixson et al. | |
| 2009/0138003 | A1 | 5/2009 | Deville et al. | |
| 2009/0149854 | A1 | 6/2009 | Cunningham et al. | |
| 2009/0171353 | A1* | 7/2009 | Johnson et al. | 606/51 |
| 2009/0240246 | A1* | 9/2009 | Deville et al. | 606/33 |
| 2009/0306660 | A1 | 12/2009 | Johnson et al. | |
| 2010/0023009 | A1 | 1/2010 | Moses et al. | |
| 2010/0130977 | A1 | 5/2010 | Garrison et al. | |
| 2010/0204697 | A1 | 8/2010 | Dumbauld et al. | |
| 2011/0009859 | A1 | 1/2011 | Livneh | |
| 2011/0034918 | A1 | 2/2011 | Reschke | |
| 2011/0054472 | A1 | 3/2011 | Romero | |
| 2011/0077648 | A1 | 3/2011 | Lee et al. | |
| 2012/0083786 | A1* | 4/2012 | Artale et al. | 606/51 |

FOREIGN PATENT DOCUMENTS

| | | |
|---|---|---|
| CN | 201299462 | 9/2009 |
| DE | 2415263 | 10/1975 |
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |

(56) References Cited

FOREIGN PATENT DOCUMENTS

| | | | |
|---|---|---|---|
| DE | 10 2008 018406 | | 7/2009 |
| EP | 1159926 | | 12/2001 |
| EP | 1 532 932 | A1 | 5/2005 |
| EP | 1532932 | | 5/2005 |
| EP | 1 609 430 | A1 | 12/2005 |
| EP | 1 645 240 | A2 | 4/2006 |
| JP | 61-501068 | | 9/1984 |
| JP | 6-502328 | | 3/1992 |
| JP | 5-5106 | | 1/1993 |
| JP | 5-40112 | | 2/1993 |
| JP | 6-030945 | | 2/1994 |
| JP | 6-121797 | | 5/1994 |
| JP | 6-285078 | | 10/1994 |
| JP | 6-343644 | | 12/1994 |
| JP | 6-511401 | | 12/1994 |
| JP | 7-265328 | | 10/1995 |
| JP | 8-56955 | | 3/1996 |
| JP | 8-317936 | | 3/1996 |
| JP | 8-289895 | | 5/1996 |
| JP | 8-252263 | | 10/1996 |
| JP | 8-317934 | | 12/1996 |
| JP | 9-10223 | | 1/1997 |
| JP | 9-122138 | | 5/1997 |
| JP | 10-24051 | | 1/1998 |
| JP | 11-070124 | | 5/1998 |
| JP | 10-155798 | | 6/1998 |
| JP | 2000-102545 | | 9/1998 |
| JP | 11-47150 | | 2/1999 |
| JP | 11-169381 | | 6/1999 |
| JP | 11-192238 | | 7/1999 |
| JP | 11-244298 | | 9/1999 |
| JP | 2000-342599 | | 12/2000 |
| JP | 2000-350732 | | 12/2000 |
| JP | 2001-8944 | | 1/2001 |
| JP | 2001-29356 | | 2/2001 |
| JP | 2001-03400 | | 4/2001 |
| JP | 2001-128990 | | 5/2001 |
| JP | 2001-190564 | | 7/2001 |
| JP | 2002-528166 | | 3/2002 |
| JP | 2003-245285 | | 9/2003 |
| JP | 2004-517668 | | 6/2004 |
| JP | 2004-528869 | | 9/2004 |
| JP | 2011-125195 | | 6/2011 |
| RU | SU401367 | | 11/1974 |
| WO | WO 00/36986 | | 6/2000 |
| WO | WO 00/59392 | | 10/2000 |
| WO | WO 01/15614 | | 3/2001 |
| WO | WO 01/54604 | | 8/2001 |
| WO | WO 2005/110264 | | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 20, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, Feb. 8, 2012, William H. Nau, Jr.
U.S. Appl. No. 13/400,290, filed Feb. 20, 2012, Eric. R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.

(56) References Cited

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing For Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Intl Search Report EP 04027479.7 dated Mar. 8, 2005.
Int'l Search Report EP 04027705.5 dated Feb. 3, 2005.
Iraq Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.

(56) References Cited

OTHER PUBLICATIONS

Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 183476.8 dated November Jan. 11, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report PCT/US2013/028286 dated Jun. 21, 2013.
Chinese Office Action dated Jul. 25, 2014 issued in Chinese Appln. No. 201110309635.6.
Chinese Office Action, and English translation, issued May 20, 2015 in Application No. CN 201110309635.6.
Extended European Search Report from Appl. No. 13757413.3 dated Sep. 14, 2015.
Chinese Office Action together with the English translation dated Mar. 4, 2016 in corresponding CN Application No. 201380019229.3.
Australian Examination Report dated Mar. 2, 2016 in corresponding AU Application No. 2014227486.

* cited by examiner

VESSEL SEALING INSTRUMENT

CROSS-REFERENCE TO RELATED APPLICATION

The present application is a continuation-in-part of a U.S. application Ser. No. 12/897,346 titled "Vessel Sealing Instrument" by Ryan C. Artale on Oct. 4, 2010, which is hereby incorporated by reference.

BACKGROUND

1. Background of Related Art

The present disclosure relates to forceps used for open surgical procedures. More particularly, the present disclosure relates to a forceps that applies electrosurgical current to seal tissue.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. It has been determined that a fused vessel wall is optimum between 0.001 and 0.006 inches. Below this range, the seal may shred or tear and above this range the lumens may not be properly or effectively sealed.

With respect to smaller vessel, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried and vessel sealing is defined as the process of liquefying the collagen in the tissue so that it reforms into a fused mass. Thus, coagulation of small vessels is sufficient to permanently close them. Larger vessels need to be sealed to assure permanent closure.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

SUMMARY

According to one aspect of the present disclosure, a bipolar electrosurgical instrument is provided. The instrument includes a housing and an elongated shaft extending from the housing. An end effector is coupled to a distal end of the elongated shaft. A handle assembly is operably coupled to the housing and includes a movable handle movable relative to a fixed handle for effecting movement of the jaw members relative to one another from a first position wherein the jaw members are disposed in spaced relation relative to one another to a second position wherein the jaw members cooperate to grasp tissue therebetween. Each jaw member is configured to connect to a source of electrosurgical energy such that the jaw members are configured to selectively conduct energy through tissue held therebetween to effect a tissue seal. A switch is disposed on the fixed handle and is configured to be depressed between a first position and at least one subsequent position upon biasing engagement with a switch engaging surface disposed on the movable handle. The first position of the switch causes the relay of information to the user corresponding to a desired pressure on tissue grasped between the jaw members and the at least one subsequent position is configured to activate the source of electrosurgical energy to supply electrosurgical energy to the jaw members.

Alternatively or in addition, a knife channel may be defined along a length of at least one of the jaw members and the electrosurgical instrument may include a cutting mechanism configured to reciprocate along the knife channel to cut tissue grasped between the jaw members.

Alternatively or in addition, the bipolar electrosurgical instrument may include an actuator for selectively advancing the cutting mechanism from a first position wherein the cutting mechanism is disposed proximal to tissue grasped between the jaw members to at least one subsequent position wherein the cutting mechanism is disposed distal to tissue grasped between the jaw members.

Alternatively or in addition, the switch may generate a first tactile response upon movement thereof to the first position and a subsequent tactile response upon movement thereof to the at least one subsequent position.

Alternatively or in addition, the desired pressure range may be measured by at least one strain gauge disposed within the forceps.

Alternatively or in addition, the first position of the switch may correspond to an initial closure pressure of the moveable handle relative to the fixed handle and the at least one subsequent position of the switch corresponds to a subsequent closure pressure of the movable handle relative to the fixed handle that is greater than the initial closure pressure.

Alternatively or in addition, the bipolar electrosurgical instrument may include a safety lockout configured to prevent reciprocation of the cutting mechanism when the jaw members are disposed in the first position.

Alternatively or in addition, each of the jaw members may include an electrically conductive sealing surface and at least one of the jaw members may include at least one non-conductive stop member disposed on the electrically conductive sealing surface configured to control the distance between opposing electrically conductive sealing surfaces when tissue is held therebetween.

According to a further aspect of the present disclosure, a bipolar electrosurgical instrument is provided. The instrument includes a housing and an elongated shaft extending from the housing. An end effector is coupled to a distal end of the elongated shaft. A handle assembly is operably coupled to the housing and includes a movable handle movable relative to a fixed handle for effecting movement of the jaw members relative to one another from a first position wherein the jaw members are disposed in spaced relation relative to one another to a second position wherein the jaw members cooperate to grasp tissue therebetween. Each jaw member is configured to connect to a source of electrosurgical energy such that the jaw members selectively conduct energy through tissue held therebetween to effect a tissue seal. A knife channel is defined along a length of at least one of the jaw members. A cutting mechanism is configured to reciprocate along the knife channel to cut tissue grasped between the jaw members. An actuator selectively advances the cutting mechanism from a first position wherein the cutting mechanism is disposed proximal to tissue grasped between the jaw members to at least one subsequent position wherein the cutting mechanism is disposed distal to tissue grasped between the jaw members. A switch is disposed on the fixed handle and is configured to be depressed between a first position and at least one subsequent position upon biasing engagement with a switch engaging surface disposed on the movable handle. The first position of the switch causes the relay of information to the user corresponding to a desired pressure on tissue grasped between the jaw members and the at least one subsequent position is configured to activate the source of electrosurgical energy to supply electrosurgical energy to the jaw members.

Alternatively or in addition, the first position of the switch may correspond to an initial closure pressure of the first and second shafts and the at least one subsequent position of the switch may correspond to a subsequent closure pressure of the first and second shafts that is greater than the initial closure pressure.

Alternatively or in addition, the bipolar electrosurgical instrument may include a safety lockout configured to prevent reciprocation of the cutting mechanism when the jaw members are disposed in the first position.

According to a further aspect of the present disclosure, a method of performing an electrosurgical procedure is provided. The method includes the step of moving a first handle relative to a second handle of a bipolar forceps to grasp tissue between first and second jaw members. The method also includes the step of depressing a switch upon movement of the first shaft relative to the second shaft to a first position to relay information to a user corresponding to a predetermined grasping pressure applied to tissue grasped between the jaw members. The method also includes the step of depressing the switch to at least one subsequent position to activate a source of electrosurgical energy to supply electrosurgical energy to the jaw members.

The method may also include the step of selectively advancing a cutting mechanism from a first position wherein the cutting mechanism is disposed proximal to tissue grasped between the jaw members to at least one subsequent position wherein the cutting mechanism is disposed distal to tissue held between the jaw members.

The method may also include the step of generating a first tactile response corresponding to the first position of the switch.

The method may also include the step of generating a second tactile response corresponding to the at least one subsequent position of the switch.

In the drawings and in the description that follows, the term "proximal", as is traditional, will refer to the end of electrosurgical instrument that is closer to the user, while the term "distal" will refer to the end that is further from the user.

BRIEF DESCRIPTION OF THE DRAWINGS

Various embodiments of the subject instrument are described herein with reference to the drawings wherein.

DETAILED DESCRIPTION

Figure 1:
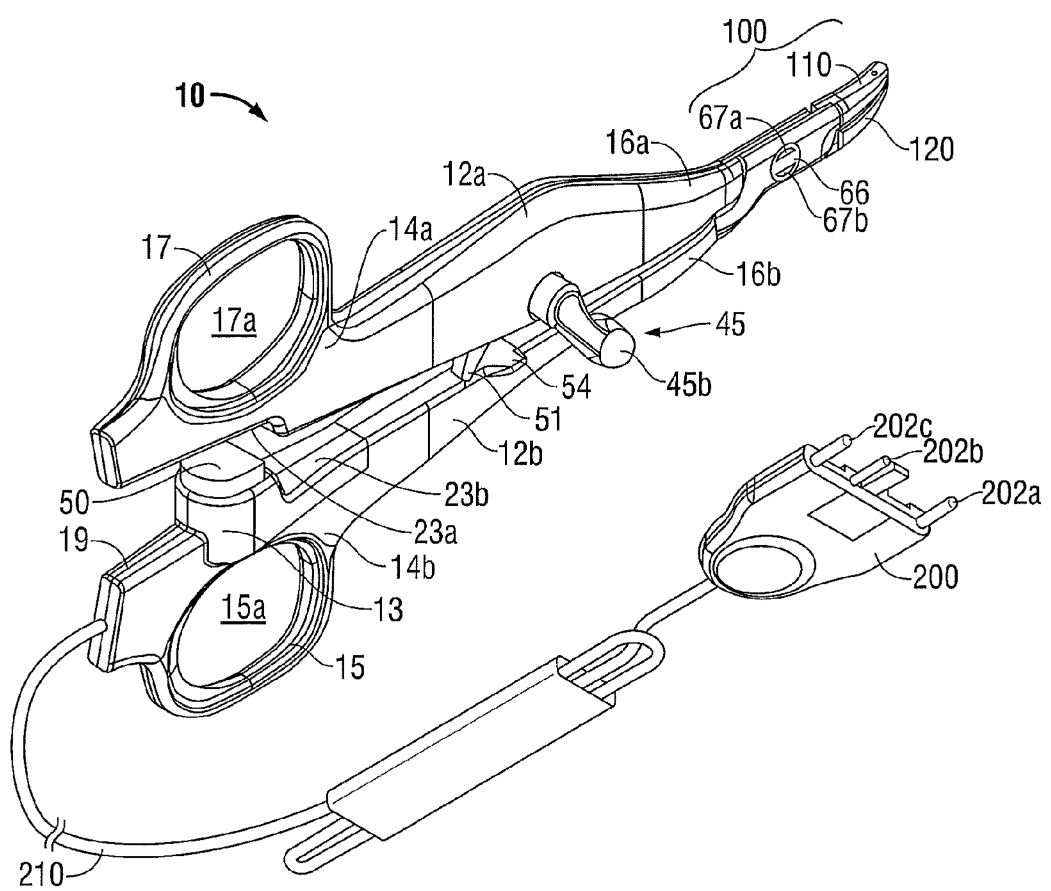
FIG. 1 is a right, perspective view of a forceps according to one embodiment of the present disclosure.
Figure 2:
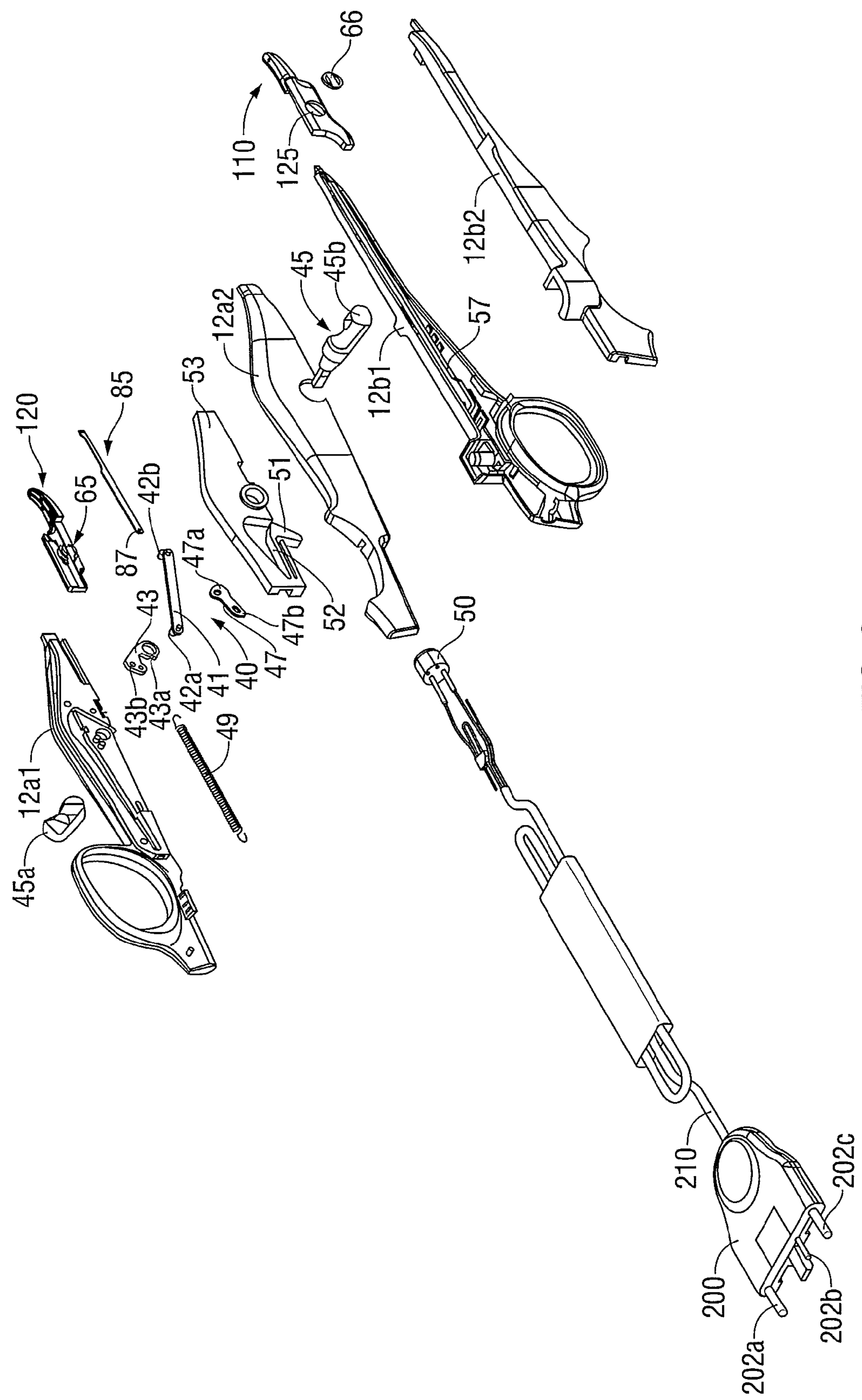
FIG. 2 is an exploded view of the forceps of FIG. 1.

Referring initially to FIGS. 1 and 2, a forceps 10 for use with open surgical procedures includes elongated shaft portions 12*a* and 12*b* each having a proximal end 14*a*, 14*b* and a distal end 16*a* and 16*b*, respectively.

The forceps 10 includes an end effector assembly 100 that attaches to the distal ends 16*a* and 16*b* of shafts 12*a* and 12*b*, respectively. The end effector assembly 100 includes pair of opposing jaw members 110 and 120 that are pivotably connected and movable relative to one another about a pivot 65 (FIG. 2) to grasp tissue. Pivot 65 is disposed on a proximal end of jaw member 120 and includes opposing halves 65*a* and 65*b* disposed on opposing sides of a channel 126 (FIG. 4C) that is configured to facilitate reciprocation of a cutting mechanism or knife 85 therethrough (FIG. 2), as discussed in detail below.

Each shaft 12*a* and 12*b* includes a handle 17 and 15, respectively, disposed at the proximal end 14*a* and 14*b* thereof. Each handle 15 and 17 defines a finger hole 15*a* and 17*a*, respectively, therethrough for receiving a finger of the user. Handles 15 and 17 facilitate movement of the shafts 12*a* and 12*b* relative to one another which, in turn, pivot the jaw members 110 and 120 from an open position wherein the jaw members 110 and 120 are disposed in spaced relation relative to one another to a clamping or closed position wherein the jaw members 110 and 120 cooperate to grasp tissue therebetween.

As best seen in FIG. 2, shaft 12*a* is constructed from two components, namely, 12*a*1 and 12*a*2, that are coupled together to form shaft 12*a*. Likewise, shaft 12*b* is constructed from two components, namely, 12*b*1 and 12*b*2, that are coupled together to form shaft 12*b*. In some embodiments, component halves 12*a*1 and 12*a*2 and component halves 12*b*1 and 12*b*2 are ultrasonically welded together at a plurality of different weld points and/or may be mechanically coupled together by any suitable method including snap-fitting, adhesive, fastened, etc.

The arrangement of shaft 12*b* is slightly different from shaft 12*a*. More particularly, shaft 12*a* is generally hollow to house the knife 85 and an actuating mechanism 40. The actuating mechanism 40 is operatively associated with a trigger 45 having handle members 45*a* and 45*b* disposed on opposing sides of shaft 12*a* to facilitate left-handed and right-handed operation of trigger 45. Trigger 45 is operatively associated with a series of suitable inter-cooperating elements (e.g., FIG. 2 shows a trigger link 43, a knife pushing link 41, a spring 49, and an anti-deployment link 47) configured to mechanically cooperate (not explicitly shown) to actuate the knife 85 through tissue grasped between jaw members 110 and 120 upon actuation of trigger 45. The spring 49 is coupled between the inner structure of shaft 12*b* and the trigger link 43. Knife pushing link 41 includes a proximal pivot pin 42*a* that is received in a friction-fit manner within a pivot aperture 43*b* defined through the trigger link 43 and a distal pivot pin 42*b* that is received in a pivot aperture 87 (FIG. 6) defined through a proximal end of knife 85. The trigger 45 is operatively associated with the trigger link 43 such that rotation of the trigger 45 overcomes the biasing force of the spring 49 to rotate the trigger link 43 in a corresponding direction. The trigger link 43 mechanically cooperates with the knife pushing link 41 to reciprocate the knife 85 through a knife channel 115 (FIG. 3B). Upon release of the trigger 45, the force of the spring 49 automatically rotates the trigger link 43 counter clock-wise to retract the knife 85 proximally.

With reference to FIG. 1, the proximal end 14*b* of shaft 12*b* includes a switch cavity 13 protruding from an inner facing surface 23*b* of shaft 12*b* and configured to seat a depressible switch 50 therein (and the electrical components associated therewith). Switch 50 aligns with an opposing inner facing surface 23*a* of the proximal end 14*a* of shaft 12*a* such that upon approximation of shafts 12*a* and 12*b* toward one another, the switch 50 is depressed into biasing engagement with the opposing inner facing surface 23*a* of the proximal end 14*a* of shaft 12*a*.

As shown in FIG. 2, the actuating mechanism 40 includes a cover 53 disposed within the shaft 12*a*. The cover 53 includes a cantilever spring 52 extending distally from a proximal end thereof. A protrusion 51 is disposed on the distal end of cantilever spring 52 and extends from inner facing surface 23*a* of shaft 12*a* toward an opposing pad 54 disposed on inner facing surface 23*b* of shaft 12*b* (FIG. 1). Upon approximation of shafts 12*a* and 12*b*, protrusion 51 is engaged by pad 54 such that protrusion 51 is biased inward by virtue of the cantilever spring 52 toward shaft 12*a* to permit further approximation of shafts 12*a* and 12*b* and biasing engagement of switch 50 by the opposing inner facing surface 23*a* of the shaft 12*a*.

As shown in FIG. 1, an electrosurgical cable 210 having a plug 200 at its proximal end connects the forceps 10 to an electrosurgical generator (not shown). More specifically, the distal end of the cable 210 is securely held to the shaft 12*b* by a proximal shaft connector 19 and the proximal end of the cable 210 includes a plug 200 having prongs 202*a*, 202*b*, and 202*c* that are configured to electrically and mechanically engage the electrosurgical generator.

The tissue grasping portions of the jaw members 110 and 120 are generally symmetrical and include similar component features that cooperate to permit facile rotation about pivot 65 to effect the grasping and sealing of tissue. As a result, and unless otherwise noted, jaw member 110 and the operative features associated therewith are initially described herein in detail and the similar component features with respect to jaw member 120 will be briefly summarized thereafter.

Figure 3A:
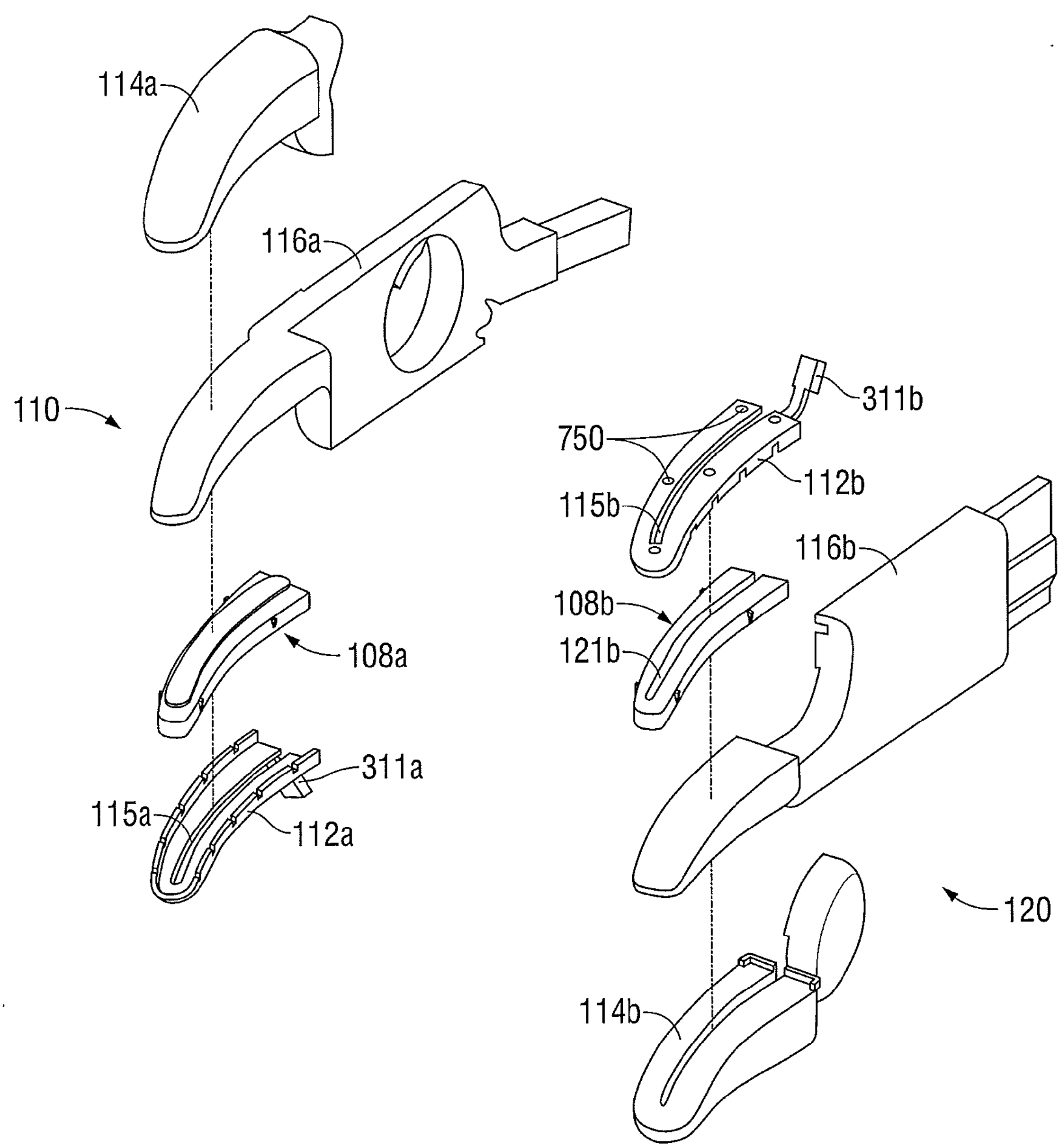
FIG. 3A is an exploded view of an end effector assembly of the forceps of FIG. 1.
Figure 3B:
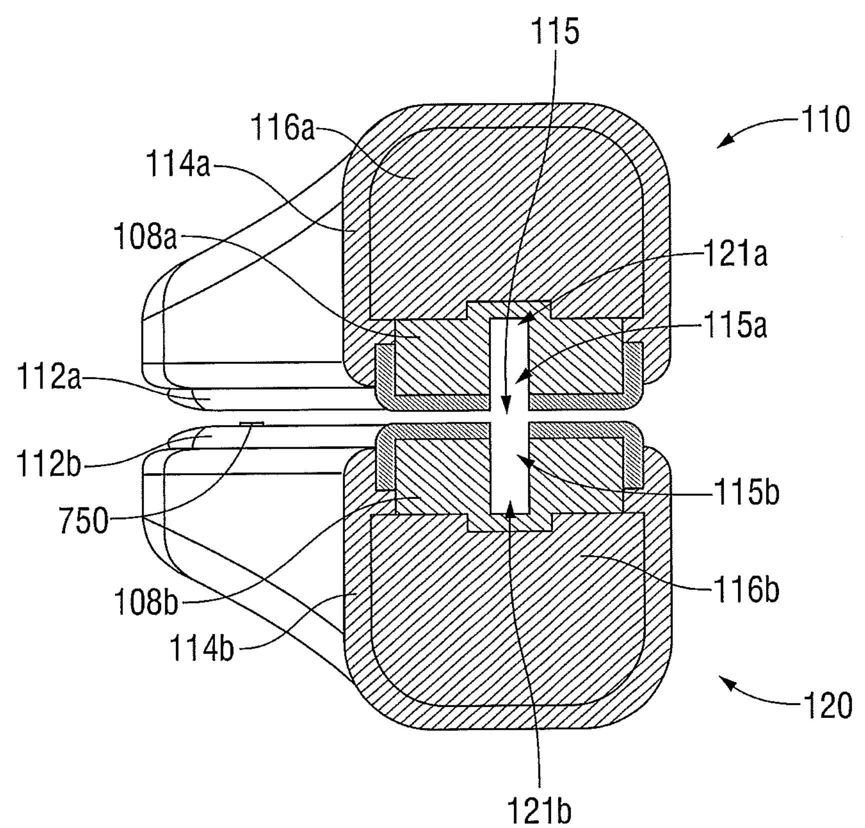
FIG. 3B is a cross-sectional view of the end effector assembly of the forceps of FIG. 1.

With reference to FIGS. 3A and 3B, jaw member 110 includes an outer housing 116*a*, first and second non-conductive plastic insulators 108*a* and 114*a*, and an electrically conductive sealing surface 112*a*. The first and second insulators 108*a* and 114*a* are overmolded about jaw housing 116*a* in a two-shot overmolding process. More specifically, the first insulator 108*a* is overmolded about jaw housing 116*a* to electrically insulate the jaw housing 116*a* from sealing surface 112*a* and the second insulator 114*a* is overmolded about jaw housing 116*a* to secure the electrically conductive sealing surface 112*a* thereto. This may be accomplished by stamping, by overmolding, by overmolding a stamped sealing surface, and/or by overmolding a metal injection molded sealing surface. The jaw members 110 and 120 are made from a conductive material. In some embodiments, the jaw members 110 and 120 are powder coated with an insulative coating to reduce stray current concentrations during sealing.

As best shown by the cross-sectional view of FIG. 3B, electrically conductive sealing surface 112*a* of jaw member 110 is pronounced from the jaw housing 116*a* and the second insulator 114*a* such that tissue is grasped by the opposing electrically conductive sealing surfaces 112*a* and 112*b* when jaw members 110 and 120 are in the closed position.

Likewise, jaw member 120 includes similar elements that correspond to jaw member 110 including: an outer housing 116*b*, first and second plastic insulators 108*b* and 114*b*, and an electrically conductive sealing surface 112*b* that is pronounced from the jaw housing 116*b* and second insulator 114*b*. As described above with respect to jaw member 110, the first insulator 108*b* electrically insulates the jaw housing 116*b* from the sealing surface 112*b* and the second insulator 114*b* secures the sealing surface 112*b* to the jaw housing 116*b*. Insulators 114*a* and 114*b* extend along the entire length of jaw members 110 and 120, respectively, to reduce alternate or stray current paths during sealing. In some embodiments, each of sealing surfaces 112*a* and 112*b* may include an outer peripheral edge that has a radius such that each insulator 114*a* and 114*b* meets the respective sealing surface 112*a* and 112*b* along an adjoining edge that is generally tangential to the radius and/or meets along the radius.

As shown in FIGS. 3A and 3B, at least one of the jaw members, e.g., jaw member 120, includes at least one stop member 750 disposed on the inner facing surfaces of the electrically conductive sealing surface 112*b* and/or 112*a*. Alternatively or in addition, the stop member(s) 750 may be disposed adjacent to the electrically conductive sealing surfaces 112*a*, 112*b* or proximate the pivot 65. The stop member(s) 750 facilitate gripping and manipulation of tissue and to define a gap between opposing jaw members 110 and 120 during sealing and cutting of tissue. In some embodiments, the stop member(s) 750 maintain a gap distance between opposing jaw members 110 and 120 within a range of about 0.001 inches (~0.03 millimeters) to about 0.006 inches (0.015 millimeters).

As shown in FIG. 2, shaft 12*b* includes a beam 57 disposed therein and extending between handle 15 and jaw member 110. In some embodiments, the beam 57 is constructed of flexible steel to allow the user to generate additional sealing pressure on tissue grasped between the jaw members 110 and 120. More specifically, once end effector assembly 100 is closed about tissue, the shafts 12*a* and 12*b* may be squeezed toward each other to utilize the flexibility of the beam 57 to generate the necessary closure pressure between jaw members 110 and 120. In this scenario, the mechanical advantage realized by the compressive force associated with the beam 57 facilitates and assures consistent, uniform, and accurate closure pressure about tissue grasped between jaw members 110 and 120 (e.g., within a working pressure range of about 3 $kg/cm^2$ to about 16 $kg/cm^2$). By controlling the intensity, frequency, and duration of the electrosurgical energy applied to the tissue, the user can seal tissue. In some embodiments, the gap distance between opposing sealing surfaces 112*a* and 112*b* during sealing ranges from about 0.001 inches to about 0.005 inches.

In some embodiments, the sealing surfaces 112*a* and 112*b* are relatively flat to avoid current concentrations at sharp edges and to avoid arcing between high points. In addition, and due to the reaction force of the tissue when engaged, each of jaw members 110 and 120 may be manufactured to resist bending, e.g., tapered along its length to provide a constant pressure for a constant tissue thickness at parallel and the thicker proximal portion of the jaw members 110 and 120 will resist bending due to the reaction force of the tissue.

As shown in FIGS. 3A, 3B, 4B, and 4C, at least one of jaw members 110 and 120 includes a knife channel 115*a* and/or 115*b*, respectively, disposed therebetween that is configured to allow reciprocation of a knife 85 therethrough. In the illustrated embodiment, a complete knife channel 115 is formed when two opposing channel halves 115*a* and 115*b* associated with respective jaw members 110 and 120 come together upon grasping of the tissue. Each plastic insulator 108*a* and 108*b* includes a trough 121*a* and 121*b*, respectively, that aligns in vertical registration with an opposing knife channel half 115*a* and 115*b*, respectively, such that knife 85 does not contact or cut through plastic insulators 108*a* and 108*b* upon reciprocation through knife channel 115. In some embodiments, the width of knife channels 115*a* and 115*b* and their respective troughs 121*a* and 121*b* may be equal along an entire length thereof.

Figure 4A:
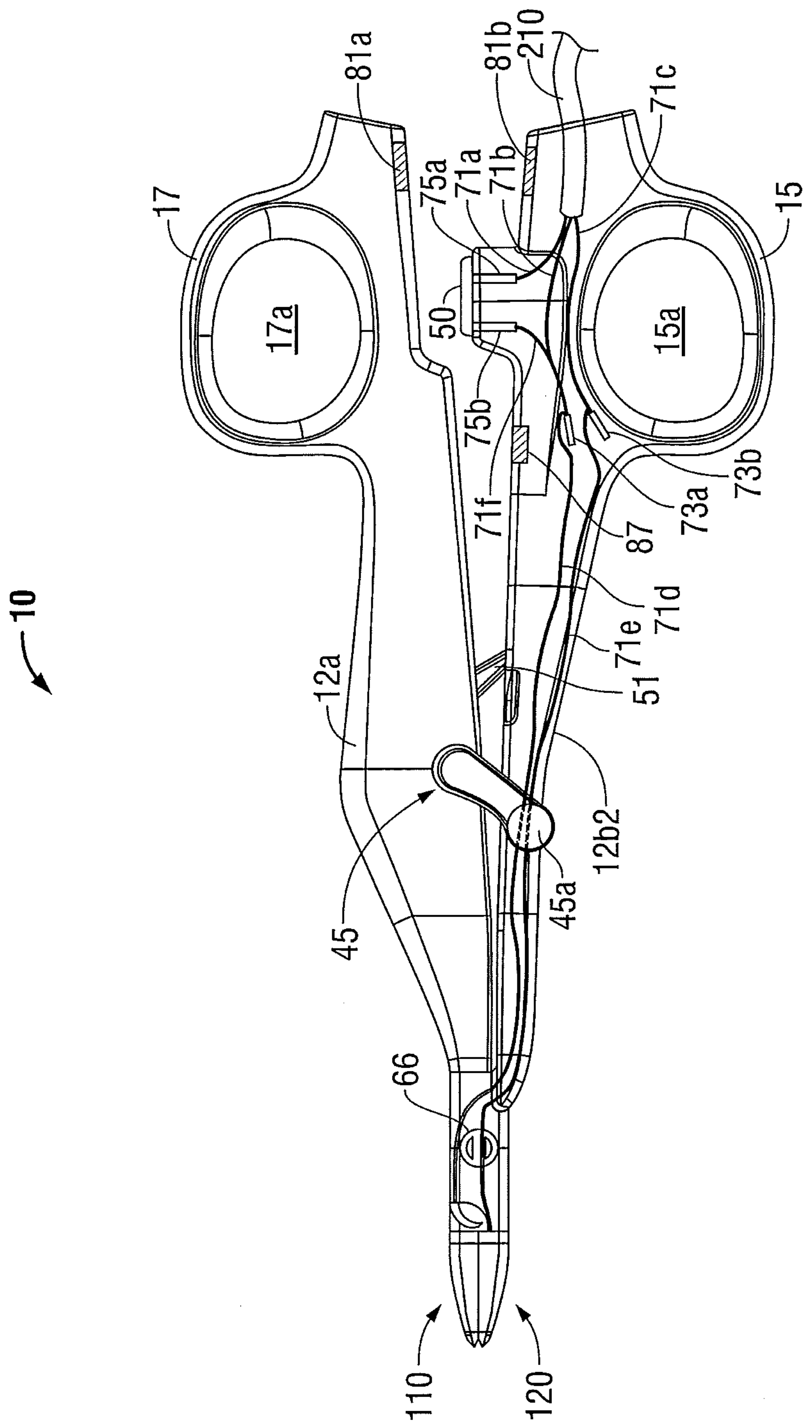
FIG. 4A is a side view of the forceps of FIG. 1 with parts partially removed to show the electrical connection between a switch and the end effector assembly.

As best shown in FIG. 4A, the interior of cable 210 houses leads 71*a*, 71*b* and 71*c*. Leads 71*a*, 71*b*, and 71*c* extend from the plug 200 through cable 210 and exit the distal end of the cable 210 within the proximal connector 19 of shaft 12*b*. More specifically, lead 71*a* is interconnected between prong 202*b* and a first terminal 75*a* of the switch 50. Lead 71*b* is interconnected between prong 202*c* and a solder sleeve 73*a* which, in turn, connects lead 71*b* to an RF lead 71*d* and to a second terminal 75*b* of the switch 50 via a connector lead 71*f*. RF lead 71*d* carries a first electrical potential of electrosurgical energy from lead 71*b* to sealing surface 112*a*. Lead 71*c* is interconnected between prong 202*a* and a solder sleeve 73*b* which, in turn, connects lead 71*c* to an RF lead 71*e*. RF lead 71*e* carries a second electrical potential of electrosurgical energy from lead 71*c* to sealing surface 112*b*.

Figure 4B:
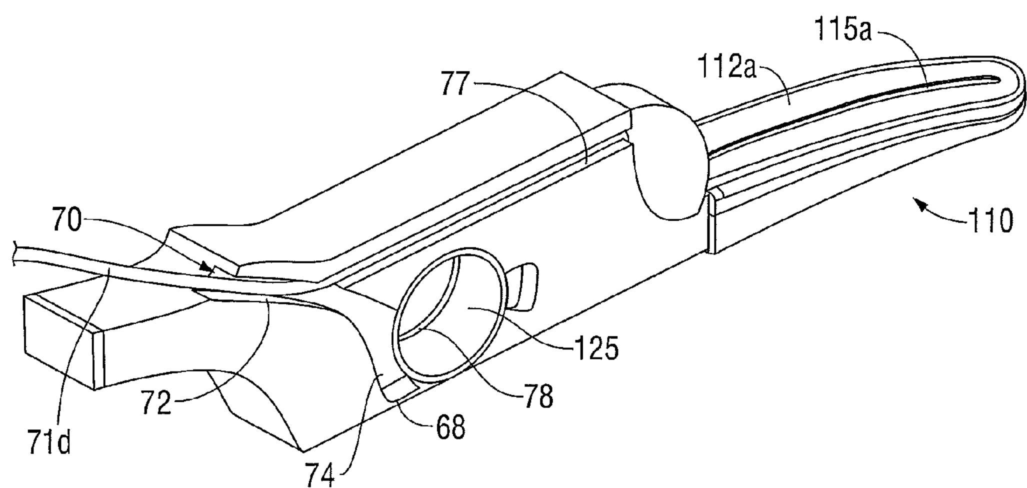
FIG. 4B is a left, perspective view of a jaw member of the end effector assembly of FIG. 1.

With reference to FIG. 4B, a lead channel 77 is defined in the proximal end of jaw member 110 to provide a pathway for lead 71*d* to connect to a junction 311*a* (FIG. 3A) extending from a proximal end of sealing surface 112*a*. A proximal end of lead channel 77 opens into a raceway 70 that includes a generally elongated configuration with a narrowed proximal end 72 and a broadened distal end 74 that defines an arcuate sidewall 68. Lead 71*d* is routed to follow a path through the proximal end 72 of raceway 70 and, further, through lead channel 77 for connection to junction 311*a*.

Figure 4C:
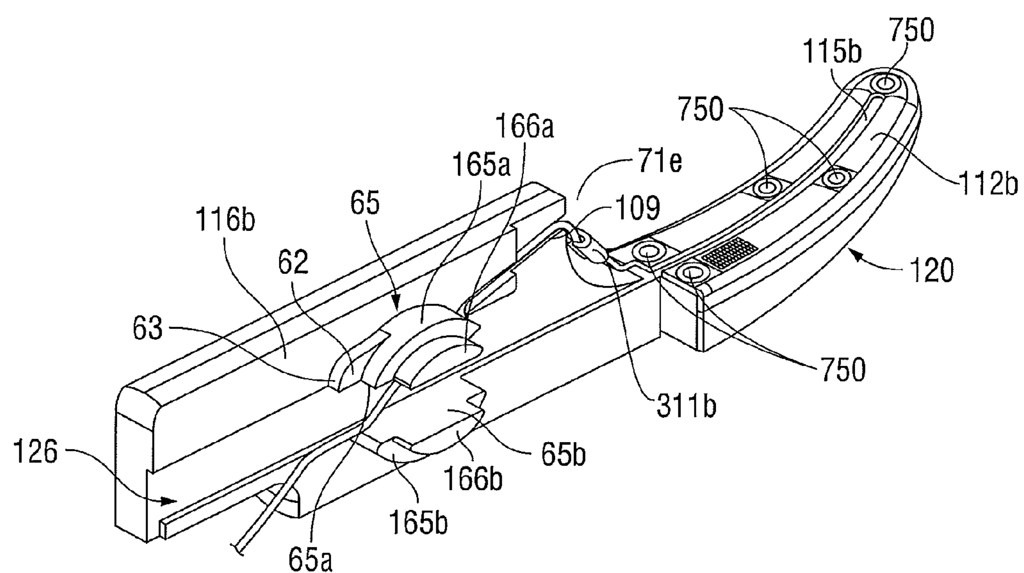
FIG. 4C is a left, perspective view of a jaw member of the end effector assembly of FIG. 1.
Figure 5A:
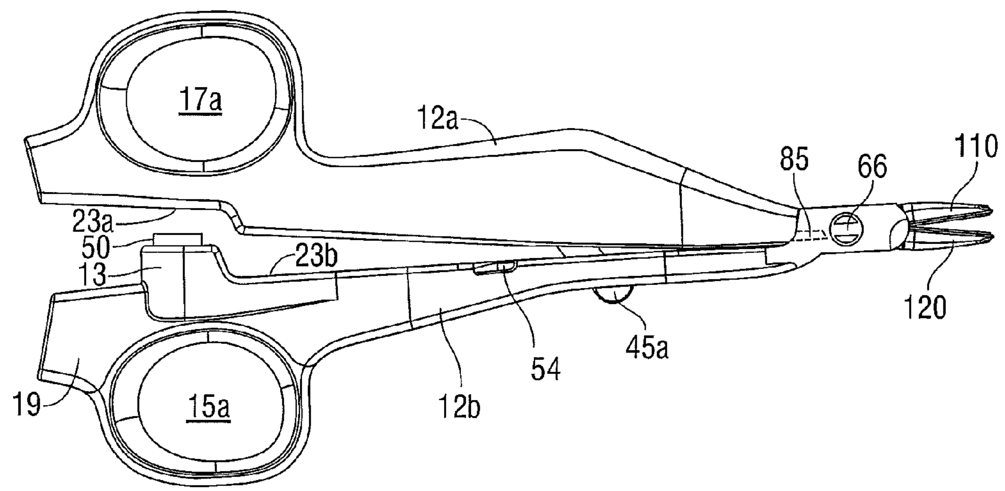
FIGS. 5A-5C are side views of the forceps of FIG. 1 illustrating actuation thereof between open and closed positions.
Figure 5B:
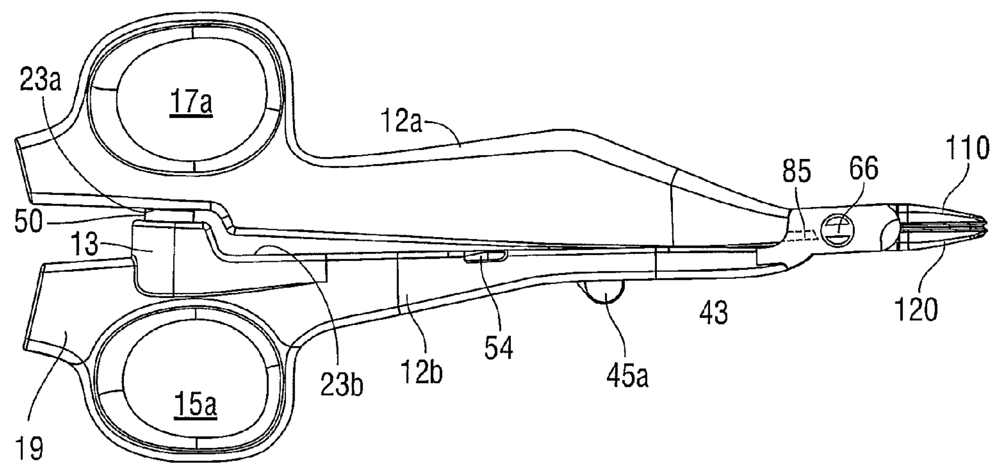
Figure 5C:
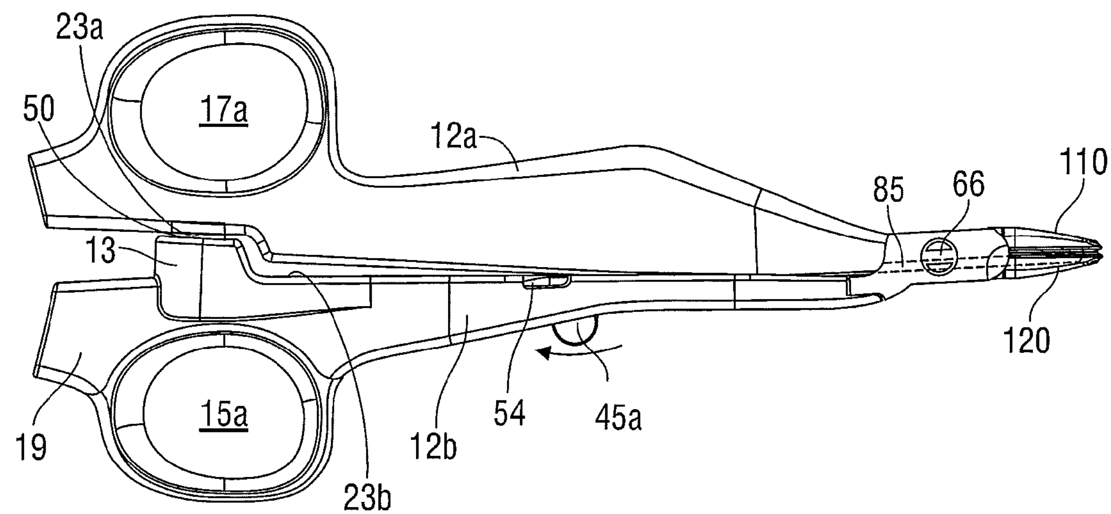

With reference to FIG. 4C, pivot halves 65*a* and 65*b* are disposed on opposing sides of channel 126 to facilitate translation of the knife 85 therethrough (FIGS. 5A-5C). Pivot halves 65*a* and 65*b* are disposed in a split spherical configuration and each include a respective base portion 165*a* and 165*b* that support an extension portion 166*a* and 166*b* thereon, respectively. Extension portions 166*a* and 166*b* are configured to engage correspondingly-dimensioned apertures 67*a* and 67*b*, respectively, disposed through a pivot plate 66 (FIG. 1) to pivotably secure jaw member 110 to jaw member 120. A lead channel 109 is defined in the proximal end of jaw member 120 to provide a pathway for lead 71*e* to connect to a junction 311*b* extending from a proximal end of sealing surface 112*b*. Lead 71*e* is routed to follow a path through raceway 70 and, further between opposing pivot halves 65*a* and 65*b* and through lead channel 109 for connection to junction 311*b*.

With reference to FIGS. 5A-5C, as the user applies closure pressure on shafts 12*a* and 12*b* to depress switch 50 (FIG. 5B), a first threshold is met corresponding to the closure force applied to switch 50 as a function of displacement of switch 50 that causes switch 50 to generate a first tactile response that corresponds to a complete grasping of tissue disposed between jaw members 110 and 120. Following the first tactile response, as the user applies additional closure pressure on shafts 12*a* and 12*b* (FIG. 5C), a second threshold is met corresponding the closure force applied to switch 50 as a function of displacement of switch 50 that causes the switch 50 to generate a second tactile response that corresponds to a signal being generated to the electrosurgical generator to supply electrosurgical energy to the sealing surfaces 112*a* and 112*b*. More specifically, the second tactile response indicates closing of a normally open circuit between switch terminals 75*a* and 75*b* and, in turn, establishment of an electrical connection between leads 71*a* and 71*b*. As a result of the electrical connection between leads 71*a* and 71*b*, the electrosurgical generator senses a voltage drop between prongs 202*b* and 202*c* and, in response thereto, supplies electrosurgical energy to sealing surfaces 112*a* and 112*b* via leads 71*d* and 71*e*, respectively.

In one embodiment, the first tactile response indicates to the user that the maximum grasping pressure has been reached before end effector 100 is energized where the user is free to approximate, manipulate, and grasp tissue as needed. In this scenario, the second tactile response indicates to the user the electrosurgical activation of the end effector 100. The switch 50 may include a plurality of other tactile responses between the above discussed first and second tactile responses and/or subsequent to the second tactile response that correspond to particular functions of the forceps 10 such as, for example, operation of the knife 85 and/or the actuation assembly 40, operation of a safety lockout mechanism associated with the actuation assembly 40, as discussed in detail below.

As shown in FIG. 4A, forceps 10 may include a gauge or sensor element 87 disposed within one or both of shafts 12*a*, 12*b* such that the clamping or grasping forces being applied to target tissue by end effector 100 may be measured and/or detected. For example, in some embodiments, sensor element 87 may be a strain gauge 87 operably associated with one or both jaw members 110, 120. Sensor element 87 may be one or more Hall effect sensors or strain gauges such as, for example, metallic strain gauges, piezoresistive strain gauges, that may be disposed within one or both of shafts 12*a* and 12*b* and/or within one or both of jaw members 110 and 120 to detect tissue pressure. Metallic strain gauges operate on the principle that as the geometry (e.g., length, width, thickness, etc.) of the conductive material changes due to mechanical stress, the resistance of the conductive material changes as a function thereof. This change in resistance is utilized to detect strain or applied mechanical stress such as, for example, the mechanical stress applied to tissue by jaw members 110 and 120. Piezoresistive strain gauges operate based on the changing resistivity of a semiconductor due to the application of mechanical stress.

Hall effect sensors may be incorporated to determine the gap between jaw members 110 and 120 based on a detected relationship between the magnetic field strength between jaw members 110 and 120 and the distance between jaw members 110 and 120.

In some embodiments, one or more reed switches 81*a*, 81*b* may be incorporated within shafts 12*a* and 12*b* to determine the proximity thereof relative to one another, as shown in FIG. 4A. More specifically, the reed switch(s) may be comprised of a switch 81*a* disposed within one of the shafts (e.g., shaft 12*a*) and a magnetic element 81*b* (e.g., electromagnet, permanent magnet, coil, etc.) disposed within the opposing shaft (e.g., shaft 12*a*) such that upon approximation of shafts 12*a* and 12*b*, the reed switch 81*a* is activated or closed by the magnetic field of the magnetic element 81*b* and, likewise, as shafts 12*a* and 12*b* are moved away from each other, the lack of magnetic field operates to deactivate or open the reed switch 81*a*. In this manner, the proximity of shafts 12*a* and 12*b* and thus, jaw members 110 and 120, may be determined based on the reaction of the reed switch 81*a* to the magnetic element 81*b*.

Any of the above discussed sensors, switches, and/or strain gauge(s) may be incorporated within an electrical circuit such that the strain detected by the strain gauge changes the electrical signal through the circuit. With this purpose in mind, an electrical circuit between the strain gauge and the switch 50 and/or an electrosurgical generator (not shown) allows communication of information such as desired tissue pressure thereto. This information may be tied to the activation of switch 50 such that the switch is not activated until a desired and/or predetermined pressure on tissue grasped between jaw members 110 and 120 is achieved as detected by the strain gauge. Accordingly, the strain gauge may be disposed strategically on the forceps 10, e.g., on one or more of jaw members 110, 120, such that pressure applied to tissue grasped between jaw members 110 and 120 affects the strain gauge.

In use, forceps 10 may be calibrated such that particular tactile responses (e.g., the first tactile response) of switch 50 corresponds to a predetermined grasping pressure on tissue as determined through use of one or more of the above discussed sensors, switches, and/or strain gauge(s). The predetermined grasping pressure about tissue is within the range of about 3 $kg/cm^2$ to about 16 $kg/cm^2$ in one embodiment and, in another embodiment, about 7 $kg/cm^2$ to about 13 $kg/cm^2$. In some embodiments, switch 50 may generate multiple tactile responses, each of which corresponds to different predetermined grasping force. For a more detailed discussion of force sensing and/or measuring devices such as load cells, strain gauges, etc., reference is made to commonly-owned U.S. application Ser. No. 11/409,154, filed on Apr. 21, 2006.

As shown in FIGS. 2, 4B, and 4C, the pivot 65 connects through an aperture 125 defined through jaw member 120 and matingly engages the pivot plate 66 seated within a circumferential lip or flange 78 (FIG. 4B) defined around the periphery of aperture 125 such that the pivot 65 is rotatably movable within the aperture 125 to move jaw members 110 and 120 between open and closed positions.

In some embodiments, actuation of the knife 85 is associated with activation of the switch 50. For example, sensor 87 may be embodied as a position sensor configured to detect the position of knife 85 relative to jaw members 110 and 120 and/or relative to tissue held therebetween. Additionally or alternatively, sensor 87 may be configured to detect either of the first and second tactile responses of switch 50 and allow or prevent actuation of the knife 85 accordingly. For example, based on feedback from the sensor 87, any one or more inter-cooperating elements or lockout mechanisms associated with the actuating mechanism 40 may be energized or de-energized to allow or prevent actuation of the knife 85, as described in more detail below.

Figure 6:
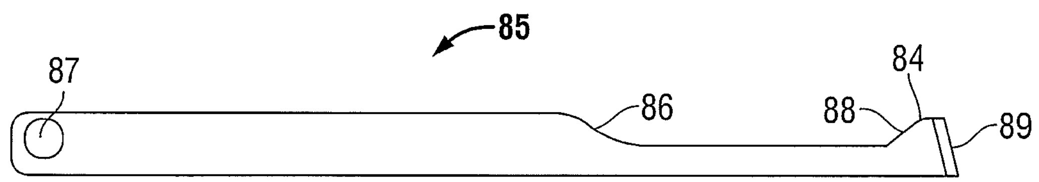
FIG. 6 is a side view of a knife for use with the forceps of FIG. 1 according to one embodiment of the present disclosure.

As shown in FIG. 6, knife 85 includes a step 86 that reduces the profile of the knife 85 toward a distal end thereof. The distal end of the knife 85 has a step 88 that increases the profile of the knife 85 toward a sharpened distal cutting edge 89. The knife 85 includes a chamfered portion 84 where the sharpened distal cutting edge 89 meets the step 88 to facilitate smooth retraction of knife 85 through the knife channel 15.

In some embodiments, the forceps 10 may include a safety lockout mechanism having a series of suitable inter-cooperating elements (e.g., anti-deployment link 47, trigger link 43) that work together to prevent unintentional firing of the knife 85 when the jaw members 110 and 120 are disposed in the open position. Generally, the anti-deployment link 47 mechanically cooperates with the trigger link 43 to prevent advancement of the knife 85 until the jaw members 110 and 120 are closed about tissue. More specifically, the anti-deployment link 47 includes an engagement tooth 47*a* formed thereon that is releasably received within a notch portion 43*a* formed in the trigger link 43 (FIG. 2) when the jaw members 110 and 120 are in the open position such that clock-wise rotation of trigger link 43 is prevented so that the knife 85 cannot be advanced distally when the jaw members 110 and 120 are in the open position (FIG. 5A). When the jaw members 110 and 120 are moved to the closed position as illustrated in FIG. 5B, the safety lockout mechanism automatically disengages to allow selective actuation of the knife 85. More particularly, a pin (not shown) disposed on protrusion 51 is received within an aperture 47*b* defined through anti-deployment link 47 to couple anti-deployment link 47 to protrusion 51. In this way, upon closure of jaw members 110 and 120, the protrusion 51 contacts the pad 54 and is biased inward toward shaft 12*b*, thereby causing counter clock-wise rotation of protrusion 51 and, in turn, clock-wise rotation of the anti-deployment link 47 such that the engagement tooth 47*a* is released from engagement with the notch portion 43*a*. Disengagement of tooth 47*a* from notch portion 43*a* allows actuation of the trigger 45 to advance the knife 85 distally through knife channel 115 to cut tissue grasped between jaw members 110 and 120. An example of a safety lockout mechanism for use with forceps 10 is described in commonly-owned U.S. application Ser. No. 12/896,100 entitled "Blade Deployment Mechanisms for Surgical Forceps", filed on Oct. 1, 2010.

In some embodiments, any one or more of the inter-cooperating elements of the safety lockout mechanism (e.g., anti-deployment link 47) may be electrically interconnected to the switch 50 and include suitable electro-mechanical components (e.g., springs, rods, solenoids, etc.) configured to be energized via activation of the switch 50 (e.g., via any one of leads 71*a*, 71*b*, 71*c*, 71*d*, 71*e*) to mechanically manipulate the safety lockout mechanism. For example, upon electrical conduction through leads 71*d* and 71*e* to energize the end effector 100, the anti-deployment link 47 is energized to cause actuation thereof such that the safety lockout mechanism disengages to allow selective actuation of the knife 85. In this scenario, by way of example, selective actuation of the knife 85 may be prevented until switch 50 has been depressed to generate at least the first tactile response.

Figure 7A:
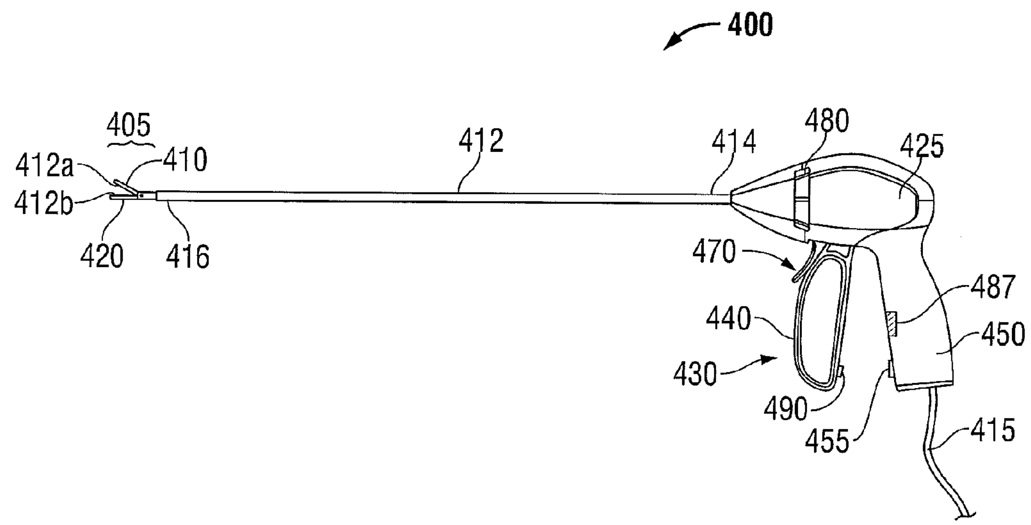
FIGS. 7A and 7B are side views of forceps according to one embodiment of the present disclosure.
Figure 7B:
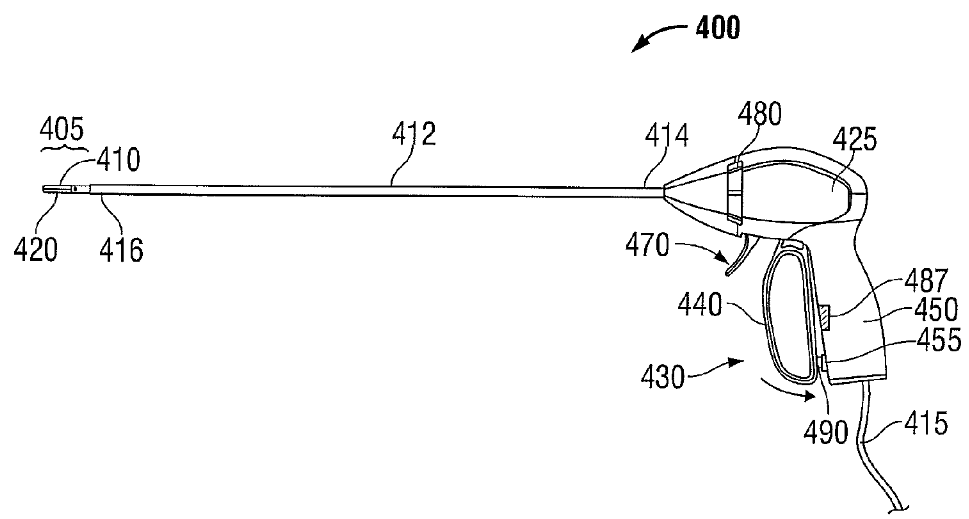

Referring now to FIGS. 7A and 7B, a forceps 400 for use with endoscopic surgical procedures is shown in accordance with embodiments of the present disclosure. Forceps 400 operates substantially as described above with respect to forceps 10 (see FIGS. 1-6) and will only be discussed to the extent necessary to describe the differences between the embodiments.

Generally, forceps 400 includes a housing 425, a handle assembly 430, a rotating assembly 480, and an end effector assembly 405 that mutually cooperate to grasp, seal, and divide tubular vessels and vascular tissue. The forceps 400 includes a shaft 412 that has a distal end 416 configured to mechanically engage the end effector assembly 405 and a proximal end 414 that mechanically engages the housing 425.

The handle assembly 430 includes a fixed handle 450 and a movable handle 440. Fixed handle 450 is integrally associated with housing 425 and handle 440 is movable relative to fixed handle 450. Rotating assembly 480 is associated with the housing 425 and is rotatable in either direction about a longitudinal axis (not shown) defined by the shaft 412. The housing 425 houses the internal working components of the forceps 400.

End effector assembly 405 is coupled to the distal end 416 of shaft 412 and includes a pair of opposing jaw members 410 and 420. Jaw members 410 and 420 each include an electrically conductive tissue sealing surface 412*a* and 412*b*, respectively, disposed thereon. Movable handle 440 of handle assembly 430 is operably associated with the end effector assembly 405 through a suitable drive assembly (not shown) to impart movement of the jaw members 410 and 420 from an open position to a clamped or closed position. The drive assembly may be any suitable combination of mechanical, electrical, and/or electromechanical components disposed within the housing 425 and configured to operably associate the movable handle 440 with the end effector assembly 405 such that movement of the movable handle 440 relative to the fixed handle 450 effects movement of the jaw members 410 and 420.

As substantially described above with respect to the jaw members 110 and 120, at least one of the jaw members 410 and 420 includes at least one stop member (not explicitly shown) disposed on the inner facing surfaces of the electrically conductive sealing surface 412*b* and/or 412*a* to facilitate gripping and manipulation of tissue and to define a gap between the jaw members 410 and 420 during sealing and cutting of tissue. For example, the stop member(s) may maintain a gap distance between the jaw members 410 and 420 of about 0.001 inches (~0.03 millimeters) to about 0.006 inches (~0.015 millimeters).

An electrosurgical cable 415 is coupled at a proximal end to the fixed handle 450 and connects the forceps 400 to an electrosurgical generator (not shown). Electrosurgical cable 415 houses a plurality of electrical leads (e.g., leads 71*a*, 71*b* and 71*c*) that cooperatively operate to supply electrosurgical energy to the electrically conductive sealing surfaces 412*a* and 412*b* as substantially described hereinabove with respect to electrosurgical cable 210 of FIG. 1.

Forceps 400 includes a switch 455 disposed on the fixed handle 450 that operates substantially as described above with respect to switch 50 of forceps 10 (see FIGS. 1-5C). Although depicted on a lower end of the fixed handle 450 in FIGS. 7A and 7B, switch 455 or a similar type switch may be disposed on any suitable location of the fixed handle 450 and, thus, FIGS. 7A and 7B are not intended to be limiting with respect to the location of switch 455 on the fixed handle 450.

The lower end of the movable handle 440 includes a switch engaging surface 490 extending therefrom. The switch engaging surface 490 is disposed on a surface of the movable handle 440 that faces the fixed handle 450. When the movable handle 440 is moved toward the fixed handle 450, the switch engaging surface 490 substantially aligns with the switch 455 such that as the moveable handle 440 is moved or squeezed toward the fixed handle 450, as indicated by the rotational arrow depicted in FIG. 7B, the switch 455 is depressed via biasing engagement with the switch engaging surface 490. As the user applies closure pressure on the moveable handle 440 to depress the switch 455 (not explicitly shown), a first threshold is met corresponding to the closure force applied to the switch 455 as a function of displacement of the switch 455 that causes the switch 455 to generate a first tactile response that corresponds to a complete grasping of tissue disposed between jaw members 410 and 420. Following the first tactile response, as the user applies additional closure pressure on the moveable handle 440 (not explicitly shown), a second threshold is met corresponding the closure force applied to the switch 455 as a function of displacement of the switch 455 that causes the switch 455 to generate a second tactile response that corresponds to a signal being generated to the electrosurgical generator to supply electrosurgical energy to the jaw members 410 and 420.

Engagement of the switch 455 by switch engaging surface 490 depresses the switch 455 to meet any one or more thresholds as a function of displacement of switch 455 that, as described above with reference to switch 50 of FIG. 1, causes the switch 455 to generate one or more tactile responses. Each tactile response corresponds to a particular condition. For example, the switch 455 may generate a first tactile response corresponding to a complete grasping of tissue sensed between jaw members 410 and 420 and a second tactile response upon additional depression of the switch 455 relative to the fixed handle 450 corresponding to a signal being generated to the electrosurgical generator to supply electrosurgical energy to the sealing surfaces 412*a* and 412*b*.

Although not explicitly shown, at least one of the jaw members 410 and 420 may include a knife channel that is configured to allow reciprocation of a knife therethrough as substantially described above with respect to the knife channel 115*a* and/or 115*b* and the knife 85 of FIGS. 1-6. Forceps 400 includes a trigger 470 operatively associated with a series of suitable inter-cooperating elements (not explicitly shown) configured to actuate the knife substantially as described above with respect to trigger 45 of FIGS. 1-6.

Substantially as described above with respect to the safety lockout mechanism of the forceps 10, forceps 400 may include a safety lockout mechanism having a series of suitable inter-cooperating elements that work together to prevent unintentional firing of the knife when the jaw members 410 and 420 are disposed in the open position. By way of example, the forceps 400 may include inter-cooperating elements such as or substantially similar to the anti-deployment link 47 and trigger link 43 described hereinabove to prevent advancement of the knife until the jaw members 410 and 420 are closed about tissue as substantially described above with respect to the safety lockout mechanism of the forceps 10. An example of a safety lockout mechanism for use with forceps 400 is described in commonly-owned U.S. application Ser. No. 12/896,100 entitled "Blade Deployment Mechanisms for Surgical Forceps," filed on Oct. 1, 2010.

In some embodiments, any one or more of the inter-cooperating elements of the safety lockout mechanism may be electrically interconnected to the switch 455 and include suitable electro-mechanical components (e.g., springs, rods, solenoids, etc.) configured to be energized via activation of the switch 455 to mechanically manipulate the safety lockout mechanism as substantially described above with respect to the switch 50 of the forceps 10.

Substantially as described above with respect to the sensor element 87 of FIG. 4A, forceps 400 may optionally include a gauge or sensor element 487 disposed within either movable handle 440 or fixed handle 450 (depicted within fixed handle 450 in FIGS. 7A and 7B for illustrative purposes) such that the clamping or grasping forces being applied to target tissue by end effector 405 may be measured. For example, in some embodiments, the sensor element 487 may be a strain gauge operably associated with one or both jaw members 410, 420.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar electrosurgical instrument, comprising:

a housing;

an elongated shaft extending from the housing and having a pair of opposed jaw members disposed at a distal end thereof;

a handle assembly operably coupled to the housing and including a movable handle movable relative to a fixed handle for effecting movement of the jaw members relative to one another between a first position wherein the jaw members are disposed in spaced relation relative to one another and a second position wherein the jaw members cooperate for grasping tissue therebetween, each jaw member configured to connect to a source of electrosurgical energy such that the jaw members are configured to selectively conduct energy through grasped tissue to effect a tissue seal, at least one of the jaw members including a knife channel defined along a length thereof;

a cutting mechanism configured to reciprocate within the knife channel;

a safety lockout configured to prevent advancement of the cutting mechanism when the jaw members are disposed in the first position; and a switch disposed on the fixed handle and configured to be depressed to a first position and at least one subsequent position upon biasing engagement with the movable handle, wherein depression of the switch to the first position generates a tactile response indicating a grasping pressure and the at least one subsequent position of the switch is configured to activate the source of electrosurgical energy, wherein the safety lockout further includes:

an anti-deployment link;

a knife pushing link having a proximal end and a distal end coupled to a proximal end of the cutting mechanism; and a trigger link coupled to the proximal end of the knife pushing link and configured to effect advancement of the cutting mechanism via the knife pushing link, wherein when the safety lockout is in a first position, the anti-deployment link is engaged with the trigger link to prevent rotation of the trigger link.

2. The bipolar electrosurgical instrument according to claim 1, wherein depression of the switch to the at least one subsequent position generates a subsequent tactile response.

3. The bipolar electrosurgical instrument according to claim 1, wherein the grasping pressure is measured by at least one strain gauge disposed within the bipolar electrosurgical instrument.

4. The bipolar electrosurgical instrument according to claim 1, wherein the first position of the switch corresponds to an initial closure pressure of the movable handle relative to the fixed handle and the at least one subsequent position of the switch corresponds to a subsequent closure pressure of the movable handle relative to the fixed handle that is greater than the initial closure pressure.

5. A bipolar electrosurgical instrument according to claim 1, wherein each of the jaw members includes an electrically conductive sealing surface and at least one of the jaw members includes at least one non-conductive stop member disposed on the electrically conductive sealing surface configured to control the distance between opposing electrically conductive sealing surfaces when the jaw members are disposed in the second position.

6. A bipolar electrosurgical instrument, comprising:

a housing;

an elongated shaft extending from the housing and having a pair of opposed jaw members disposed at a distal end thereof;

a handle assembly operably coupled to the housing and including a movable handle movable relative to a fixed handle for effecting movement of the jaw members relative to one another between a first position wherein the jaw members are disposed in spaced relation relative to one another and a second position wherein the jaw members cooperate for grasping tissue therebetween, each jaw member configured to connect to a source of electrosurgical energy such that the jaw members are configured to selectively conduct energy through grasped tissue to effect a tissue seal;

a knife channel defined along a length of at least one of the jaw members;

a cutting mechanism configured to reciprocate within the knife channel to cut tissue grasped between the jaw members;

an actuator for selectively advancing the cutting mechanism between a first position wherein the cutting mechanism is disposed proximal to the knife channel and at least one subsequent position wherein the cutting mechanism is disposed within the knife channel;

a safety lockout configured to prevent advancement of the cutting mechanism when the jaw members are disposed in the first position; and a switch disposed on the fixed handle and configured to be depressed to a first position and at least one subsequent position upon biasing engagement with the movable handle, wherein depression of the switch to the first position generates a tactile response indicating a grasping pressure and the at least one subsequent position of the switch is configured to activate the source of electrosurgical energy, wherein the safety lockout further includes:

an anti-deployment link;

a knife pushing link having a proximal end and a distal end coupled to a proximal end of the cutting mechanism; and a trigger link operatively associated with the actuator and coupled to the proximal end of the knife pushing link such that actuation of the actuator effects advancement of the cutting mechanism via the knife pushing link and the trigger link, wherein when the safety lockout is in a first position, the anti-deployment link is engaged with the trigger link to prevent rotation of the trigger link.

7. The bipolar electrosurgical instrument according to claim 6, wherein the first position of the switch corresponds to an initial closure pressure of the movable handle relative to the fixed handle and the at least one subsequent position of the switch corresponds to a subsequent closure pressure of the movable handle relative to the fixed handle that is greater than the initial closure pressure.

* * * * *